Sept. 18, 1934. P. DOT Plant Pat. 102
ROSE
Filed Dec. 28, 1933
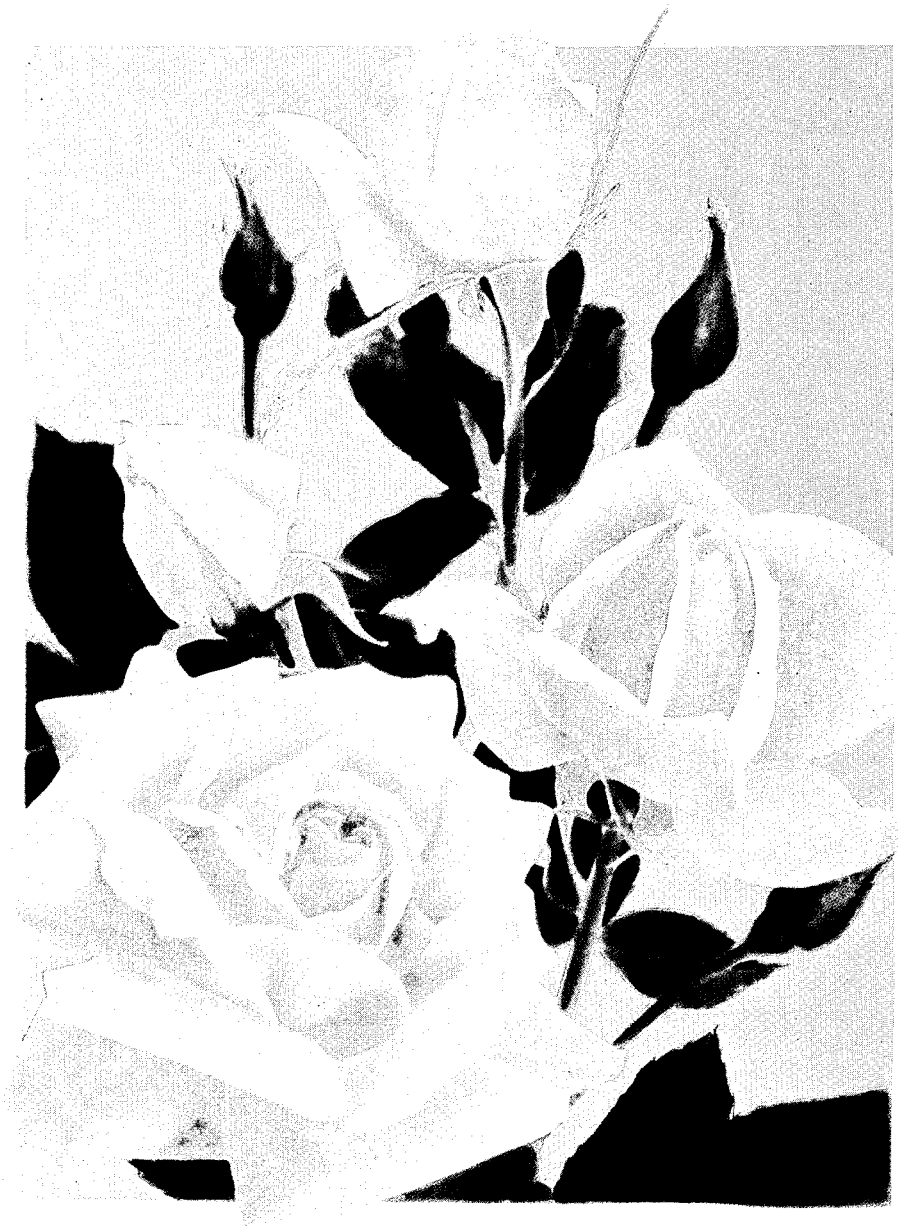
Inventor
Pedro Dot
By Robbe & Robbe
M. A. Macdonald
Attorneys Patented Sept. 18, 1934

Plant Pat. 102

UNITED STATES PATENT OFFICE

102

ROSE

Pedro Dot, San Feliu de Llobregat, near Barcelona, Spain, assignor to The Conard-Pyle Company, West Grove, Pa.

Application December 28, 1933, Serial No. 704,357

1 Claim. (Cl. 47—61)

This invention relates to a new variety of rose, the result of definite breeding in a successful effort to produce a new color in roses suitable for cut flowers.

This new rose was produced by crossing the Hybrid Tea rose, Mme. Butterfly, and the Pernetiana Hybrid rose, Federico Casas; Mme. Butterfly was used as the female or seed parent, and Federico Casas as the male or pollen parent.

This new rose has inherited the best characters of both parents, the fine form and long stems of Mme. Butterfly and new color and upright growth from Federico Casas.

The plant of this new rose puts out new canes from the base of the plant and new lateral shoots with greater freedom than any other rose plant with which I am familiar.

The dominant features of novelty of this new rose are found in the color characteristics of the bloom hereinafter specifically described, in the refreshing fragrance of the new mown hay through all its development and in its unusual quantity of bloom produced continuously during the growing season. The new plant has been asexually reproduced; the distinct characteristics herein set forth were transmitted true to form and appear to be permanently fixed.

The following is a detailed description of this rose plant and its flower, all references to color being based on the Royal Horticultural Society's Color Chart.

Parentage:—
Seedling.
*Seed parent.*—Mme. Butterfly.
*Pollen parent.*—Federico Casas.
Classification:—
Pernetiana Hybrid, usually commercially classed as Hybrid Tea.

*Flower*

Blooming habit:
*Recurrent.*—Continuous.
Bud:
*Size.*—Large.
*Form.*—Ovoid, pointed.
*Color.*—Orange copper with veining and markings of carmine.
*Sepals.*—Branched, with foliate ends, fold back.
*Calyx.*—Wide and shallow, like a shallow cup. Smooth fruit fragrance when rubbed.
*Peduncle.*—Medium length, quite rough, strong. Color: reddish light green.
*Opening.*—Opens well, not affected by weather conditions.
Bloom:—
*Size.*—Large 3½ to 4½ inches.
*Borne.*—Usually singly; sometimes in clusters.
*Stems.*—Long, strong.
*Form.*—High center, keeping the stamens covered.
*Petalage.*—About 50 petals.
*Color.*—Orange copper when first opening, gradually a shade of pink overspreads the copper and orange, making a new rose color. When fully blown the color is soft old rose flushed with gold, with an extra heavy gold flush on the lower part of the petals. Over all this is an opalescent luster which changes the color shades in different lights.
*Texture.*—Thick, leathery petals.
*Appearance.*—Inside, satiny; outside, metallic.
*Form.*—Pear shaped.
*Arrangement.*—Loosely formed.
*Persistence.*—Drop off cleanly.
*Fragrance.*—Refreshing, like new mown hay.
*Lasting quality.*—Lasts well both on the plant and as a cut flower.
Genital organs:
*Stamens, anthers.*—Numerous; stamens pink; anthers yellow.
Color:
*Pollen.*—Yellow.
*Styles.*—Loose, uneven length, slender. Extend above the stamens.
*Stigmas.*—Flesh colored.
*Ovaries.*—Several above calyx rim.
Fruit:
*Form.*—Round.
*Size.*—Natural.
*Color at maturity.*—Nasturtium to Flame (Nicolas Manual Color Chart Plate II).
*Sepals.*—Five in number.
*Seed.*—About 20.

*Plant*

Form.—Bush.
Growth.—Upright, very compact.
Foliage:
*Leaflets.*—Generally 5; sometimes only 3.
*Size.*—Medium.
*Quantity.*—Abundant.
*Color.*—New foliage, upper side pale green tinged with bronze; under side bronzy green. Mature foliage, upper side light green; under side pale green.
*Shape.*—Long, fairly narrow.
*Texture.*—Leathery; upper side dull flat; under side rough. Ribs and veins ordinary.
*Edge.*—Serrated.

*Leaf stem.*—Color green, under side prickles.

*Stipules.*—Long, serrated edges and long pointed tips which curl.

Wood:

*New wood.*—Color, light green; base slightly rough and covered with short stiff hairs.

*Old wood.*—Color, light green; base slightly wrinkled. No hairs.

Thorns:

*Quantity.*—Variable, some canes very close together, other canes widely spaced.

*Form.*—Wide bases, medium length, almost horizontal.

*Color when young.*—Pinkish pale green.

*Position.*—Uneven.

For purposes of convenience, I will now set forth a comparison of my present new variety of hybrid rose plant with its parents, hereinbefore mentioned, in order that the distinctions therefrom may be more readily discerned.

In comparison with Mme. Butterfly, the bud of my variety is ovoid in form, and orange copper in color; that of Mme. Butterfly is slender and pale pink in color. The open flower of my variety is full to the center with about fifty petals and is orange copper overspread with a pink luster; that of Mme. Butterfly is pale pink with a yellow base to the petals and slightly deeper pink on the reverses; it has about 30 petals and an open center. The flower of my variety is at least an inch greater in diameter than that of Mme. Butterfly. My variety has the fragrance of new mown hay; Mme. Butterfly has a rich sweet perfume. The plant of my variety is about twice as large as that of Mme. Butterfly.

In comparison with Federico Casas, the bud of my variety is ovoid in form, and orange copper in color; that of Federico Casas is straight and the color is copper and orange. The open flower of my variety is full to the center with about 50 petals and is orange copper overspread with a pink luster; that of Federico Casas has an open center and is copper and orange, the orange being separate at the base of the petals inside and covering most of the outside, and has about 25 petals. My variety has the fragrance of new mown hay; Federico Casas is almost scentless. The bloom of my variety is about an inch greater in diameter than Federico Casas. The plant of my variety is a little taller and is more branching than that of Federico Casas.

I claim:—

The new variety of rose as shown and described, characterized by the distinct color of its fragrant flowers through all stages of their development, and its unusual quantity of bloom produced continuously during the growing season.

PEDRO DOT.